US012686854B2

(12) United States Patent
Zhao et al.

(10) Patent No.: US 12,686,854 B2
(45) Date of Patent: Jul. 21, 2026

(54) METHOD FOR ENHANCING SECRETORY FUNCTION OF MESENCHYMAL STEM CELLS AND APPLICATION THEREOF

(71) Applicant: SHANDONG UNIVERSITY, Shandong (CN)

(72) Inventors: Shidou Zhao, Jinan (CN); Zijiang Chen, Jinan (CN); Yingying Qin, Jinan (CN); Wenlin Jiao, Jinan (CN)

(73) Assignee: SHANDONG UNIVERSITY, Shandong (CN)

( * ) Notice: Subject to any disclaimer, the term of this patent is extended or adjusted under 35 U.S.C. 154(b) by 940 days.

(21) Appl. No.: 17/794,299

(22) PCT Filed: Jul. 2, 2021

(86) PCT No.: PCT/CN2021/104328
§ 371 (c)(1),
(2) Date: Jul. 21, 2022

(87) PCT Pub. No.: WO2022/052605
PCT Pub. Date: Mar. 17, 2022

(65) Prior Publication Data
US 2023/0077870 A1　　Mar. 16, 2023

(30) Foreign Application Priority Data
Sep. 11, 2020　(CN) ......................... 202010954795.5

(51) Int. Cl.
*A61P 15/00* (2006.01)
*A61K 35/28* (2015.01)
*C12N 5/0775* (2010.01)

(52) U.S. Cl.
CPC ............ *C12N 5/0668* (2013.01); *A61K 35/28* (2013.01); *A61P 15/00* (2018.01); *C12N 2501/905* (2013.01)

(58) Field of Classification Search
CPC ............ C12N 2501/905; C12N 5/0665; C12N 5/0668; A61K 35/28
See application file for complete search history.

(56) References Cited

FOREIGN PATENT DOCUMENTS

| CN | 104958319 | A | * | 10/2015 |
|----|-----------|---|---|---------|
| CN | 105861425 | A | | 8/2016 |
| CN | 108685948 | A | | 10/2018 |
| CN | 109106727 | A | | 1/2019 |
| CN | 109852584 | A | | 6/2019 |
| CN | 110257491 | A | | 9/2019 |
| CN | 110478368 | A | | 11/2019 |
| CN | 112048469 | A | | 12/2020 |
| WO | 2013/009102 | A3 | | 4/2013 |

OTHER PUBLICATIONS

WIPO translation of CN109852584. (Year: 2019).*
Dicker KT, Gurski LA, Pradhan-Bhatt S, Witt RL, Farach-Carson MC, Jia X. Hyaluronan: a simple polysaccharide with diverse biological functions. Acta Biomater. Apr. 2014;10(4):1558-70. doi: 10.1016/j.actbio.2013.12.019. Epub Dec. 18, 2013. PMID: 24361428; PMCID: PMC3960342. (Year: 2013).*
Snetkov P, Zakharova K, Morozkina S, Olekhnovich R, Uspenskaya M. Hyaluronic Acid: The Influence of Molecular Weight on Structural, Physical, Physico-Chemical, and Degradable Properties of Biopolymer. Polymers (Basel). Aug. 11, 2020;12(8):1800. doi: 10.3390/polym12081800. (Year: 2020).*
Yoon SY. Mesenchymal stem cells for restoration of ovarian function. Clin Exp Reprod Med. Mar. 2019;46(1):1-7. doi: 10.5653/cerm.2019.46.1.1. Epub Mar. 1, 2019. (Year: 2019).*
Choudhery MS, Badowski M, Muise A, Harris DT. Comparison of human mesenchymal stem cells derived from adipose and cord tissue. Cytotherapy. Mar. 2013;15(3):330-43. doi: 10.1016/j.jcyt.2012.11.010. Epub Jan. 11, 2013. PMID: 23318344. (Year: 2013).*
Nie WB, Zhang D, Wang LS. Growth Factor Gene-Modified Mesenchymal Stem Cells in Tissue Regeneration. Drug Des Devel Ther. Mar. 26, 2020;14:1241-1256. doi: 10.2147/DDDT.S243944. PMID: 32273686; PMCID: PMC7105364. (Year: 2020).*
Aug. 12, 2021 International Search Report issued in International Patent Application No. PCT/CN2021/104328.
Aug. 12, 2021 Written Opinion issued in International Patent Application No. PCT/CN2021/104328.
Shang, Qingqing, "Experimental Study on Injectable Tissue Engineering Constructs for Improving Cardiac Function After Myocardial Infarction," Medicine and Health Science, Chinese Master's Theses Full-text Database, No. 1, Dec. 16, 2014.
Hanson, Summer E. et al., "The Effect of Mesenchymal Stromal Cell-Hyaluronic Acid Hydrogel Constructs on Immunophenotype of Macrophages," Tissue Engineering Part A, vol. 17, No. 19-20, Oct. 31, 2011, pp. 2463-2471.
Dec. 16, 2021 Office Action issued in Chinese Patent Application No. 202010954795.5.
Apr. 6, 2022 Office Action issued in Chinese Patent Application No. 202010954795.5.
Mei et al., "Sodium hyaluronate as scaffold material of rabbit bone marrow stromal cells after osteoblast induction", Chinese Journal of Anatomy, vol. 32, No. 2, 2009, pp. 152-154 and 179.
Zhang et al., "Effect of paracrine and over—expression VEGF165 of bone marrow mesenchymal stem cell under the intervention of sodium hyaluronate culture", Orthopedic Journal of China, vol. 22, No. 9, May 2014, pp. 839-842.
Zhao, Lin, "Clinical application of mesenchymal stem cells in the treatment of premature ovarian failure", Journal of Dalian Medical University, vol. 42, No. 4, 2020, pp. 289-294.

* cited by examiner

*Primary Examiner* — Christopher M Babic
*Assistant Examiner* — Qinhua Gu
(74) *Attorney, Agent, or Firm* — Oliff PLC

(57) ABSTRACT

A method for enhancing the secretory function of mesenchymal stem cells and application thereof, belonging to the field of biotechnology. The present invention finds that the secretory function of umbilical cord mesenchymal stem cells (UCMSCs) can be remarkably promoted by pretreating the UCMSCs in vitro using sodium hyaluronate (HA), including increasing the secretion of cytokines such as HGF, SCF, EGF and VEGF, promoting activation of the PI3K-AKT signaling pathway and enhancing the repair of injury.

6 Claims, 4 Drawing Sheets

Control    VCD

VCD+MSC-CM    VCD+HA/MSC-CM

METHOD FOR ENHANCING SECRETORY FUNCTION OF MESENCHYMAL STEM CELLS AND APPLICATION THEREOF

CROSS-REFERENCES TO RELATED APPLICATIONS

This application claims priority benefits to Chinese Patent Application No. 202010954795.5, filed 11 Sep. 2020, the contents of which are incorporated herein by reference.

TECHNICAL FIELD

The present invention relates to a method for enhancing secretory function of mesenchymal stem cells and application thereof, and belongs to the field of biotechnology.

BACKGROUND

Information of the Related Art part is merely disclosed to increase the understanding of the overall background of the present invention, but is not necessarily regarded as acknowledging or suggesting, in any form, that the information constitutes an existing technology that has been known to those generally skilled in the art.

Stem cells have great development potential and clinical application value in tissue engineering, disease treatment and other fields. Mesenchymal stem cells (MSCs) are widely found in connective tissues and interstitium of the whole body, and they are widely studied and applied as adult stem cells. In recent years, MSCs have become one of the important research directions in biomedical field.

Existing studies have shown that MSCs can function in various ways such as cell differentiation, paracrine and cell contact regulation. Among them, paracrine means that MSCs act on target cells and play a regulatory role by secreting cytokines, extracellular vesicles, microRNAs and other substances. Stem cells can promote cell proliferation, inhibit apoptosis, promote angiogenesis and anti-fibrosis through paracrine, and thus promote the repair and regeneration of injured tissues. It has been reported that MSCs can promote the repair of gastric mucosa, skin, ovary and other tissue injuries by activating the PI3K-Akt signalling pathway through a paracrine mechanism.

At present, one of the criteria for high-quality MSCs is that the cells have strong paracrine ability. Researchers have tried to pretreat stem cells through cytokines, growth factors, hypoxia, gene modification and other ways to enhance their paracrine function, thus improving the therapeutic effect of stem cells to a certain extent. However, the inventors found that these methods are still in the research stage, some factors are relatively expensive, and the appropriate concentration and treatment time need to be further explored; hypoxia pretreatment requires special culture equipment, and the conditions are relatively rigorous; and gene modification will change the genome of cells, and its safety needs to be further clarified. Therefore, it is still necessary to find a simple, safe and effective method that can enhance the secretory function of MSCs.

SUMMARY

In view of the above deficiencies of the prior art, the present invention provides a method for enhancing the secretory function of MSCs and application thereof. The present invention finds that the secretory function of umbilical cord mesenchymal stem cells (umbilical cord mesenchymal stem cells, UCMSCs) can be remarkably enhanced by pretreating the UCMSCs in vitro using sodium hyaluronate (HA), and the method is simple, convenient, low in cost and high in safety, and therefore has great potential for practical application.

The technical solution of the present invention is described as follows.

A first aspect of the present invention is to provide an application of HA in enhancing the secretory function of MSCs. Through research, the present invention shows that a pretreatment in vitro with HA has a good effect on promoting the secretion of MSCs. Meanwhile, hyaluronic acid is an important component of the extracellular matrix and has good biological safety and histocompatibility.

The application includes at least any one or more of the following:

(1) promoting the secretion of cytokines;

(2) promoting activation of the PI3K-AKT signaling pathway;

(3) enhancing the repair of injury.

A second aspect of the present invention is to provide a method for enhancing the secretory function of MSCs, comprising pretreating and cultivating the MSCs in a medium containing HA.

Through research, the present invention shows that a pretreatment of stem cells in vitro using a suitable concentration of HA can significantly enhance the secretory function of stem cells.

Enhanced paracrine components can further activate the PI3K-AKT signaling pathway and promote the survival of germ cells after mouse ovarian injury. The method is simple, safe, feasible and has great application potential.

The beneficial technical effects of the above one or more technical solutions include:

The above technical solution provides a simple, safe and effective method for promoting the secretory function of stem cells in vitro. Through research, the method has a good effect on enhancing the secretory function of stem cells and promoting secretion of HGF, SCF, EGF, VEGF and other factors by adding a suitable concentration of HA during culture in vitro and treating for a certain period of time. Furthermore, the method can promote the activation of the PI3K-AKT signaling pathway, and enhance the repair of ovarian injury, so it has good practical application value.

BRIEF DESCRIPTION OF THE DRAWINGS

The accompanying drawings forming a part of the present invention are used to provide further understanding of the present invention, and the exemplary embodiments of the present invention and their descriptions are used to explain the present invention, and do not constitute an improper limitation of the present invention.

DETAILED DESCRIPTION

Figure 1:
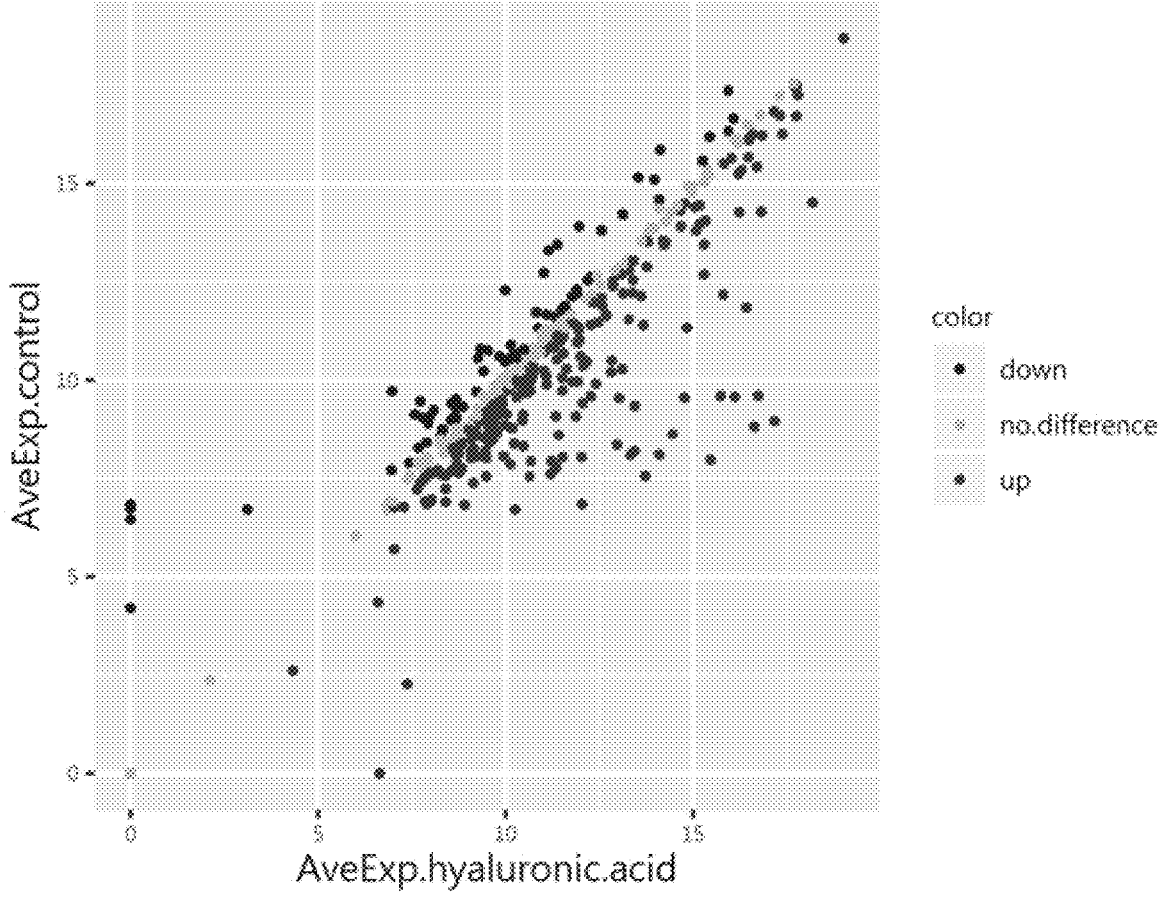
FIG. 1 is the scatter diagram of 440 cytokines array detecting the conditioned medium of MSCs by sandwich antibody array method in Example 1 of the present invention.

It should be pointed out that the following detailed descriptions are all illustrative and are intended to provide further descriptions of the present invention. Unless otherwise specified, all technical and scientific terms used in the present invention have the same meanings as those usually understood by a person of ordinary skill in the art to which the present invention belongs.

It should be noted that the terms used herein are merely used for describing specific implementations, and are not intended to limit exemplary implementations of the present disclosure. As used herein, the singular form is also intended to include the plural form unless the context clearly dictates otherwise. In addition, it should further be understood that, terms "comprise" and/or "include" used in this specification indicate that there are features, steps, operations, devices, components, and/or combinations thereof. It should be understood that the protection scope of the present invention is not limited to the following specific embodiments; it should also be understood that the terms used in the embodiments of the present invention are describing specific embodiments, rather than limiting the protection scope of the present invention. In the following specific embodiments, if the experimental methods of specific conditions are not indicated, they generally follow the conventional methods and conditions of molecular biology within the technical field of the art, and such techniques and conditions are fully explained in the literature. See, eg, Sambrook et al., Molecular Cloning: A Laboratory Manual, for techniques and conditions, or as suggested by the manufacturer.

As mentioned above, methods to promote the secretory function of MSCs are limited and have certain limitations and safety concerns.

In view of that above, the present invention finds that the secretory function of MSCs can be significantly enhanced by pretreating MSCs in vitro with HA at an appropriate concentration. The enhanced paracrine components can further activate the PI3K-AKT signaling pathway and promote the survival of germ cells after mouse ovarian injury. The method is simple, safe, feasible and has great application potential.

In an exemplary embodiment of the present invention, the application of HA in enhancing the secretory function of MSCs is provided. Experimental results of one or more embodiments of the present invention show that the secretion of MSCs is well promoted by using HA to pretreat MSCs in vitro, and hyaluronic acid is an important component of the extracellular matrix and has good biological safety and histocompatibility. In a specific embodiment of the present invention, HA is a commercial cross-linked HA gel.

The application includes at least any one or more of the following:

(1) promoting the secretion of cytokines;
(2) promoting activation of the PI3K-AKT signaling pathway;
(3) enhancing the repair of injury.

In one embodiment of the present invention, the cytokines include at least one or more selected from the group consisting of HGF, SCF, EGF and VEGF.

In one embodiment of the present invention, the injury is ovarian tissue injury; more specifically, enhancing the repair of injury is to promote germ cell survival after ovarian injury in mice.

In one embodiment of the present invention, the concentration of the HA is 0.1 to 0.3 mg/mL (preferably 0.3 mg/mL). The HA at this range of concentration can promote the secretion of stem cells without obvious negative effect on the cultured stem cells in vitro.

In another specific embodiment of the present invention, the MSCs can be derived from umbilical cord, bone marrow, fat, umbilical cord blood, endometrium, amniotic membrane, placenta or dental pulp; preferably, the MSCs are human umbilical cord mesenchymal stem cells (hUCMSCs).

In one embodiment of the present invention, a method for promoting the secretory function of stem cells is provided, which comprises pretreating and cultivating the MSCs in a medium containing HA. As a result of one or more embodiments of the present invention, it has been found that the secretory function of MSCs can be significantly enhanced by pre-treating MSCs in vitro with an appropriate concentration of HA. The enhanced paracrine components can further activate the PI3K-AKT signaling pathway and promote germ cell survival after mouse ovarian injury. The method is simple, safe, feasible and has great application potential.

Wherein, the MSCs can be derived from umbilical cord, bone marrow, fat, umbilical cord blood, endometrium, amniotic membrane, placenta or dental pulp; preferably, the MSCs are hUCMSCs.

The concentration of HA is 0.1 to 0.3 mg/mL, preferably 0.3 mg/mL.

The pretreating and cultivating is carried out for 3 to 5 days, preferably 5 days.

The present invention is further explained and illustrated by the following embodiments, but it does not constitute a limitation of the present invention. It should be understood that these embodiments are only intended to illustrate the present invention and not to limit the scope of the present invention. In addition, molecular biology methods that are not described in detail in the embodiments are conventional methods in the art, and specific operations can be found in the molecular biology guide or product manual. The cell culture conditions in the following embodiments were 37° C., 5% $CO_2$, and saturated humidity.

The Main Materials Used in Each Embodiment are as Follows:

1. Gong Ankang (cross-linked sodium hyaluronate gel for uterine cavity, specification: 5 mg/mL, manufacturer: BioRegen Biomedical (Changzhou) Co., Ltd., medical device registration certificate No.: CFDA (approval) 20153641542): 2. MEM-alpha medium (GIBCO, 12571-063); 3. Serum substitute (Helios, HPCFDCRL05); 4. ELISA kit (Thermo, ebioscience); 5. Ultrafiltration centrifuge tube (3 KDa, Millipore, UFC900308); 6. p-AKT, AKT antibody (Cell Signaling Technology, #9271, #9272), DDX4 antibody (Abcam, ab27591); 7. Embedded cell culture chamber (Sigma, PICMORG50); 8. VCD (4-vinylcyclohexene diepoxide, Sigma, 94956); 9. DMEM/F12 (1:1) medium (GIBCO, 11320-033); 10. Leibovitz's L-15 medium (GIBCO, 11415064); 11. ITS liquid media supplement (Sigma, 13146); 12. Protein extraction kit (Invent, SD-001/SN-002); 13. T75 culture flask (Corning, 430641); 14. Trizol (Ambion, 15596018).

Wild-type C57BL/6 neonatal mice were purchased from the Experimental Animal Center of Shandong University. hUCMSCs were prepared in Center for Reproductive Medicine of Shandong University.

Example 1: Detection of the Effect of HA on the Secretory Function of Stem Cells Using Cytokine Arrays S1. The same number of UCMSCs was cultured in normal medium or medium supplemented with 0.3 mg/mL HA for five days, and the medium was changed on the third day, and then the culture was continued.

S2. After five days, the two groups of cells were replaced with 13 mL of basal medium without serum substitutes, and the two groups of UCMSCs-CMs were collected after culturing in an incubator for 48 hours.

S3. After the UCMSCs-CM was centrifuged at 1500×g, filtered through a 0.22 μM filter, and centrifuged at 5000×g for 50 min at room temperature through a 3 KDa ultrafiltration centrifuge tube, the concentrated conditioned medium was collected for subsequent experiments.

S4. The concentrated conditioned medium from both groups were sent to Raybiotech Co., Ltd. for cytokine array (Raybiotech, GSH-CAA-440) analysis, and scatter plot analysis and KEGG pathway analysis of differentially expressed protein were performed.

Figure 2:
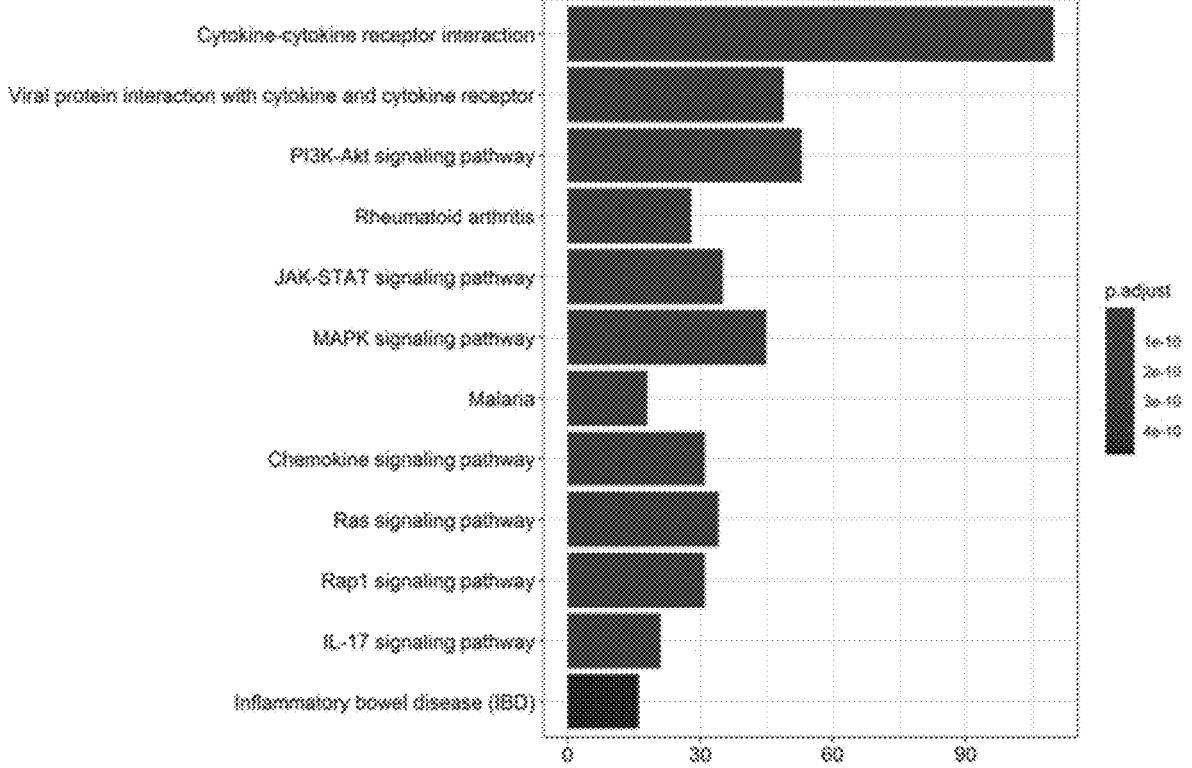
FIG. 2 is the KEGG pathway analysis result of differentially expressed proteins of cytokine array in Example 1 of the present invention.

The changes of cytokines in the two groups are shown in FIG. 1. After the MSCs were pretreated with HA, the secretory function was significantly enhanced. The results of the enrichment analysis of KEGG pathway were shown in FIG. 2. After HA pretreatment, differentially expressed cytokines secreted by UCMSCs were enriched in PI3K-AKT, JAK-STAT, MAPK and other signaling pathways.

Example 2: ELISA Method to Verify the Results of Cytokine Array

The concentrated conditioned medium was collected as described in Example 1. The MSCs-conditioned medium (MSC-CM) of the control group and the MSCs-CM of the group with HA pretreatment (HA/MSC-CM) were sent to Beijing Northern Biotechnology Research Institute Co., Ltd. for ELISA detection, and the cytokines to be validated included HGF, VEGF, EGF, and SCF.

Figure 3:
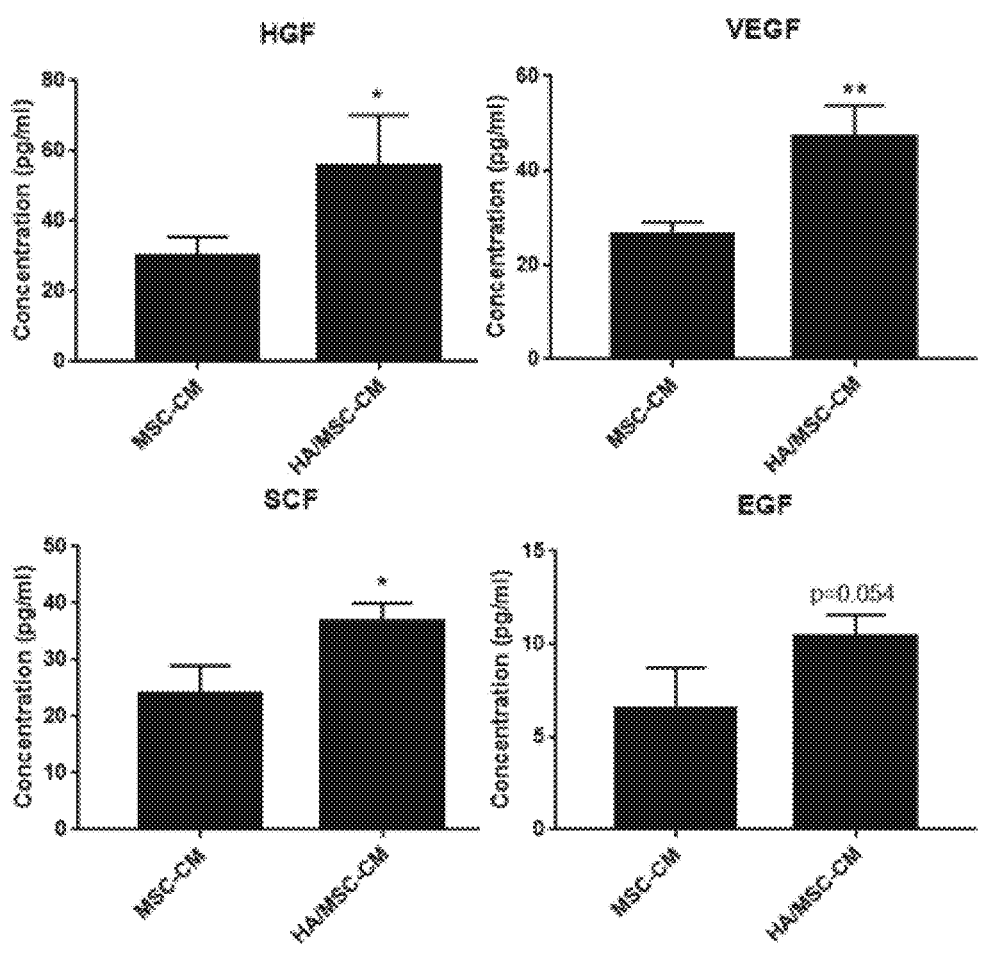
FIG. 3 is the result of differentially expressed cytokines analyzed by ELISA assay in Example 2 of the present invention.

As shown in FIG. 3, the secretion of cytokines including HGF, VEGF, EGF and SCF increased after HA pretreatment, which was consistent with the array results.

Example 3: Ovaries were Cultured In Vitro to Detect the Effect of HA-Pretreated MSCs-CM on Activation of the PI3K-AKT Pathway S1. The concentrated conditioned medium was collected as described in Example 1.

S2. The solution for dissecting ovary containing 10% FBS and 1% penicillin-streptomycin was prepared in L15 medium.

S3. Ovarian culture preparation was performed. The medium of control group, VCD (30 μM) group, VCD+ MSC-CM group and VCD+HA/MSC-CM group were prepared, and the embedded culture chamber was placed in 6-well plate containing 1.5 mL medium per well for 2 hours.

S4. The ovaries of postnatal day 4 (PD4) mice were isolated in freshly prepared dissecting solution under stereoscope. The surrounding tissues and ovarian capsule were gently peeled off, which should move quickly and not damage ovarian tissues.

S5. The obtained ovaries were washed three times with dissecting solution and transferred to an operation table as soon as possible. Before the ovaries were placed in the chambers of each group, the ovaries were washed three times with the corresponding medium of each group. After washing, they were placed in the middle of the culture chambers of each group and placed at intervals. The solution was changed on the second day. After 4 days of in vitro culture, the ovarian tissues were collected to extract protein.

S6. The changes of the expression of p-AKT and AKT protein were detected by Western blot.

Figure 4:
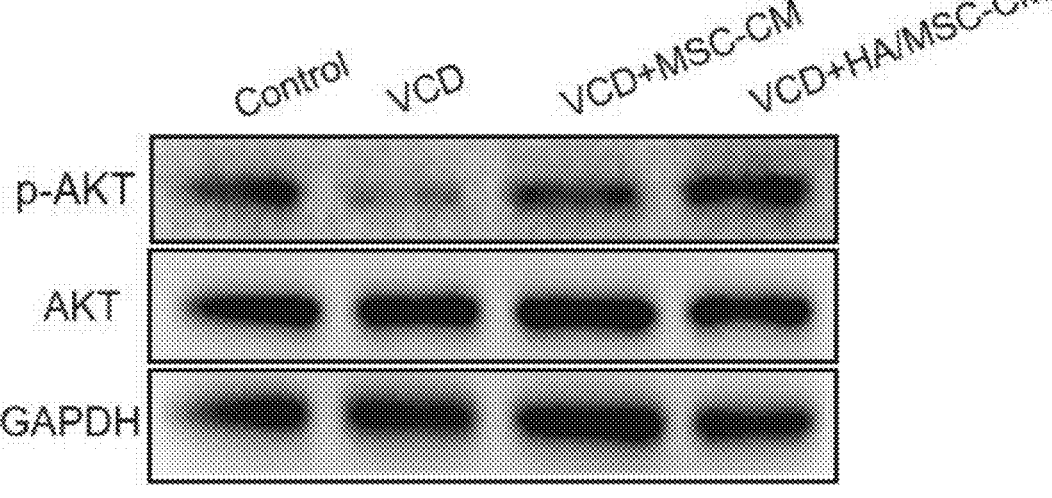
FIG. 4 shows the activation of the PI3K-AKT pathway in mouse ovaries after 4 days of in vitro culture which was facilitated by using HA pretreatment of UCMSCs conditioned medium (UCMSCs-CM) in Example 3 of the present invention.

As shown in FIG. 4, there was a certain level of p-AKT expression in the ovary of the control group, and the expression level of p-AKT decreased significantly after VCD injury; MSCs-CM could reverse the decrease in p-AKT induced by VCD injury to a certain extent. Compared with the MSCs-CM without HA pretreatment, the MSCs-CM with HA pretreatment has a stronger rescue effect on VCD damage. The expression level of AKT protein in each group was almost unchanged.

Example 4: Ovaries were Cultured In Vitro to Detect the Effect of MSCs-CM on Germ Cell Survival after HA Pretreatment The concentrated conditioned medium was collected as described in Example 1, and the ovary was cultured in vitro as described in Example 3. The ovaries were cultured in vitro for 8 days, then collected, fixed in Bouin's solution, dehydrated in gradient, embedded and sectioned. Immunohistochemical staining was performed on the sections of each group, and DDX4, a marker of germ cells, was stained. The sections of each group were observed and photographed under a microscope.

Figure 5:
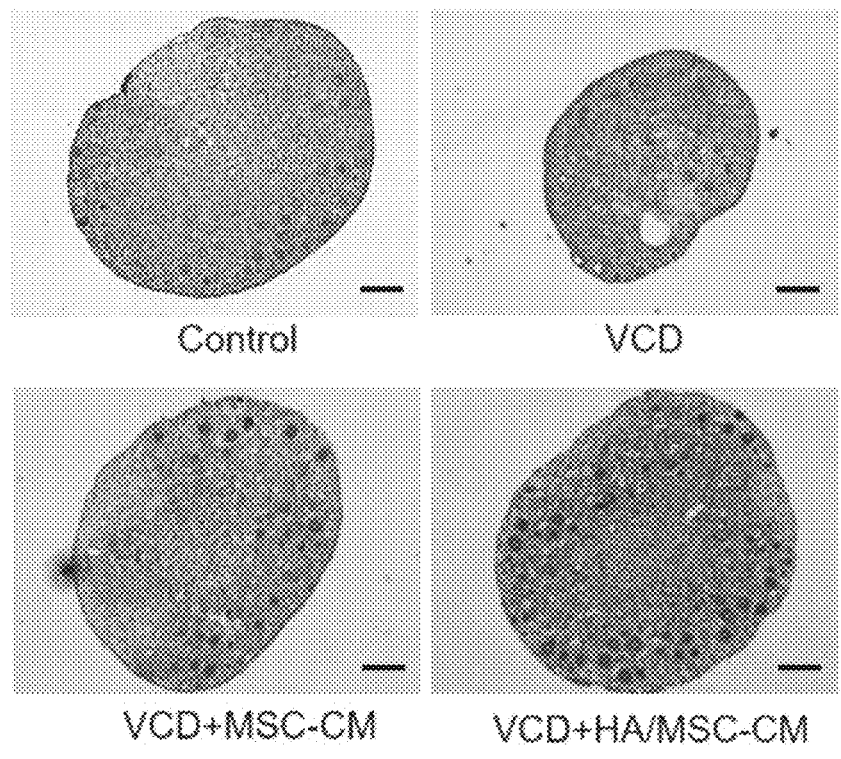
FIG. 5 shows that more germ cells were rescued in mouse ovaries after 8 days of in vitro culture which was facilitated by using HA pretreatment of UCMSCs-CM in Example 4 of the present invention.

As shown in FIG. 5, there were a large number of germ cells in normal cultured ovaries. After VCD injury, the number of germ cells decreased significantly and the ovarian volume decreased. Compared with the MSCs-CM without HA pretreatment, the HA pretreatment further enhanced the rescue of VCD-injured germ cells by MSCs-CM and increased germ cells survival.

Example 5: Effect of HA Pretreatment on mRNA Expressions of MSCs Gene was Detected by RNA-Seq S1. The same number of UCMSCs was cultured in normal medium or medium supplemented with 0.3 mg/mL HA for five days, and the medium was changed on the third day, and then the culture was continued.

S2. On the fifth day, the culture medium was discarded, the cells were washed with PBS for three times, and then 1 ml of trypsin was added for digestion. After 30 s, 5 ml of culture medium was added to terminate the digestion. Centrifugation was performed at 1000 rpm for 5 min, and 1 ml Trizol was added to the cell precipitation and sent to Shandong Xiuyue Biotechnology Co., Ltd. for RNA sequencing using Illumina novaseq 6000 platform.

Figure 6:
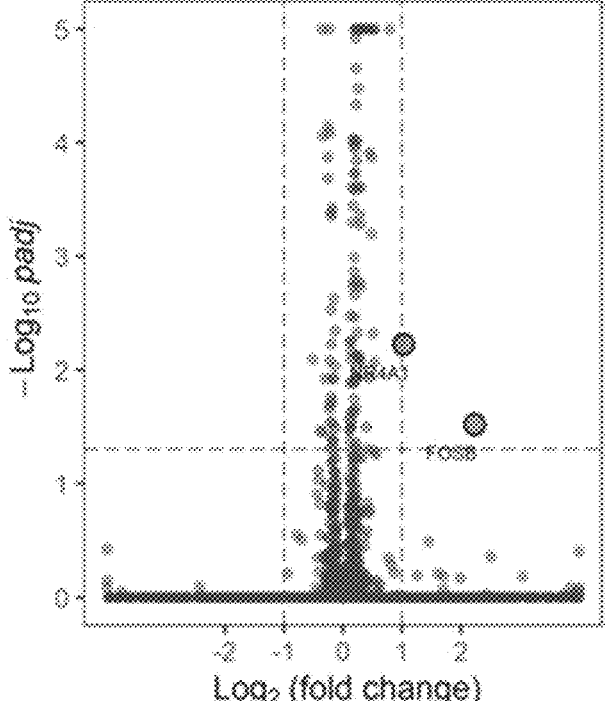
FIG. 6 is a volcano plot shows the expression changes in mRNA level of HA-treated UCMSCs detected by RNA sequencing (RNA-seq) in Example 5 of the present invention.

As shown in FIG. 6, a total of 29,207 expressed genes were detected at the mRNA level by RNA sequencing. According to the standard of $p_{adj} < 0.05$ and $|log_2FC| \geq 1$, there were only two differentially expressed genes between the two groups (FOSB and NR4A1), both of which were up-regulated genes after HA pretreatment (the fold change of FOSB was 2.03; the fold change of NR4A1 was 4.70), and the expression abundance of these two genes was low, suggesting that HA pretreatment had no significant effect on the mRNA expression of genes in MSCs.

It should be noted that the above embodiments are only used to illustrate the technical solutions of the present invention but not to limit them. Although the present invention has been described in detail with reference to the given embodiments, those skilled in the art can modify or equivalently replace the technical solutions of the present invention as required without departing from the spirit and scope of the technical solutions of the present invention.

What is claimed is:

1. A method of enhancing secretory function of mesenchymal stem cells comprising administering a composition consisting of sodium hyaluronate to the mesenchymal stem cells, wherein:

the mesenchymal stem cells are human umbilical cord mesenchymal stem cells;

the concentration of sodium hyaluronate is 0.1-0.3 mg/ml;

the composition is administered for 3 to 5 days; and the administration results in promoting the secretion of cytokines from the mesenchymal stem cells.

2. The method of claim 1, wherein the concentration of sodium hyaluronate sodium is 0.3 mg/mL.

3. The method of claim 1, wherein the composition is administered for 5 days.

4. The method according to claim 1, wherein, following the administration of the composition, the mesenchymal stems cells promote repair of an injury by activating of the PI3K-AKT signaling pathway through a paracrine mechanism.

5. The method according to claim 4, wherein the injury is ovarian tissue injury.

6. The method according to claim 1, wherein the cytokines comprise HGF, SCF, EGF and VEGF.

* * * * *